(12) United States Patent
Luo et al.

(10) Patent No.: US 7,608,167 B2
(45) Date of Patent: *Oct. 27, 2009

(54) CROSSLINKED CARBOXYALKYL CELLULOSE FIBERS HAVING PERMANENT AND NON-PERMANENT CROSSLINKS

(75) Inventors: Mengkui Luo, Tacoma, WA (US); S. Ananda Weerawarna, Seattle, WA (US); Jian Qin, Appleton, WI (US); James H Wiley, Tacoma, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 355 days.

This patent is subject to a terminal disclaimer.

(21) Appl. No.: 11/537,881

(22) Filed: Oct. 2, 2006

(65) Prior Publication Data

US 2008/0082064 A1    Apr. 3, 2008

(51) Int. Cl.
*D21F 11/00*    (2006.01)

(52) U.S. Cl. .......................... 162/158; 162/157.2; 162/9; 162/78; 525/54.3; 524/13

(58) Field of Classification Search ................. 162/158, 162/157.2, 9, 12, 78, 181.4, 164.1, 184; 525/54.3; 524/13, 14, 35

See application file for complete search history.

(56) References Cited

U.S. PATENT DOCUMENTS

| | | |
|---|---|---|
| 5,137,537 A | 8/1992 | Herron et al. |
| 5,183,707 A | 2/1993 | Herron et al. |
| 5,190,563 A | 3/1993 | Herron et al. |
| 5,998,511 A | 12/1999 | Westland et al. |

*Primary Examiner*—Mark Halpern
(74) *Attorney, Agent, or Firm*—John M. Crawford

(57) ABSTRACT

Substantially water-insoluble, water-swellable, non-regenerated, carboxyalkyl cellulose fibers, wherein the fibers have a surface having the appearance of the surface of a cellulose fiber, and wherein the fibers include a plurality of non-permanent intra-fiber metal crosslinks and a plurality of permanent intra-fiber crosslinks; and fiber bundles that include the fibers.

18 Claims, 6 Drawing Sheets

CROSSLINKED CARBOXYALKYL CELLULOSE FIBERS HAVING PERMANENT AND NON-PERMANENT CROSSLINKS

BACKGROUND OF THE INVENTION

Personal care absorbent products, such as infant diapers, adult incontinent pads, and feminine care products, typically contain an absorbent core that includes superabsorbent in a fibrous matrix. Superabsorbents are water-swellable, generally water-insoluble absorbent materials having a liquid absorbent capacity of at least about 10, preferably of about 20, and often up to about 100 times their weight in water. While the core's liquid retention or storage capacity is due in large part to the superabsorbent, the core's fibrous matrix provides the essential functions of liquid wicking, pad strength and integrity, and some amount of absorbency under load. These desirable properties are attributable to the fact that the matrix includes cellulosic fibers, typically wood pulp fluff in fiber form.

For personal care absorbent products, U.S. southern pine fluff pulp is used almost exclusively and is recognized worldwide as the preferred fiber for absorbent products. The preference is based on the fluff pulp's advantageous high fiber length (about 2.8 mm) and its relative ease of processing from a wetlaid pulp sheet to an airlaid web. However, these fluff pulp fibers can absorb only about 2-3 g/g of liquid (e.g., water or bodily fluids) within the fibers' cell walls. Most of the fibers' liquid holding capacity resides in the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak acquired liquid because liquid is not effectively retained in such a fibrous absorbent core.

The inclusion of absorbent materials in a fibrous matrix and their incorporation into personal care products is known. The incorporation of superabsorbent materials into these products has had the effect of reducing the products' overall bulk while at the same time increasing its liquid absorbent capacity and enhancing skin dryness for the products' wearers.

A variety of materials have been described for use as absorbent materials in personal care products. Included among these materials are natural-based materials such as agar, pectin, gums, carboxyalkyl starch and carboxyalkyl cellulosic, such as carboxymethyl cellulose. Natural-based materials tend to form gels rather than maintaining a solid form and are therefore not favored in these products. Synthetic materials such as polyacrylates, polyacrylamides, and hydrolyzed polyacrylonitriles have also been used as absorbent materials in personal care products. Although natural-based absorbing materials are well known, these materials have not gained wide usage in personal care products because of their relatively inferior absorbent properties compared to synthetic absorbent materials such as polyacrylates. The relatively high cost of these materials has also precluded their use in consumer absorbent products. Furthermore, many natural-based materials tend to form soft, gelatinous masses when swollen with a liquid. The presence of such gelatinous masses in a product's core tends to limit liquid transport and distribution within the core and prevents subsequent liquid insults from being efficiently and effectively absorbed by the product.

In contrast to the natural-based absorbents, synthetic absorbent materials are generally capable of absorbing large quantities of liquid while maintaining a relatively non-gelatinous form. Synthetic absorbent materials, often referred to as superabsorbent polymers (SAP), have been incorporated into absorbent articles to provide higher absorbency under pressure and higher absorbency per gram of absorbent material. Superabsorbent polymers are generally supplied as particles having a diameter in the range from about 20-800 microns. Due to their high absorbent capacity under load, absorbent products that include superabsorbent polymer particles provide the benefit of skin dryness. Because superabsorbent polymer particles absorb about 30 times their weight in liquid under load, these particles provide the further significant advantages of thinness and wearer comfort. In addition, superabsorbent polymer particles are about half the cost per gram of liquid absorbed under load compared to fluff pulp fibers. For these reasons it is not surprising that there is a growing trend toward higher superabsorbent particle levels and reduced levels of fluff pulp in consumer absorbent products. In fact, some infant diapers include 60 to 70 percent by weight superabsorbent polymer in their liquid storage core. From a cost perspective, a storage core made from 100 percent superabsorbent particles is desirable. However, as noted above, such a core would fail to function satisfactorily due to the absence of any significant liquid wicking and distribution of acquired liquid throughout the core. Furthermore, such a core would also lack strength to retain its wet and/or dry structure, shape, and integrity.

Another drawback of synthetic superabsorbent polymers is their lack of ability to biodegrade. The synthetic polymers' non-biodegradability is disadvantageous with regard to the disposal of used absorbent products containing these polymers.

Cellulosic fibers provide absorbent products with critical functionality that has, to date, not been duplicated by particulate superabsorbent polymers. Superabsorbent materials have been introduced in synthetic fiber form seeking to provide a material having the functionality of both fiber and superabsorbent polymer particle. However, these superabsorbent fibers are difficult to process compared to fluff pulp fibers and do not blend well with fluff pulp fibers. Furthermore, synthetic superabsorbent fibers are significantly more expensive than superabsorbent polymer particles and, as a result, have not competed effectively for high volume use in personal care absorbent products.

Cellulosic fibers have also been rendered highly absorptive by chemical modification to include ionic groups such as carboxylic acid, sulfonic acid, and quaternary ammonium groups that impart water swellability to the fiber. Although some of these modified cellulosic materials are soluble in water, some are water-insoluble. However, none of these highly absorptive modified cellulosic materials possess the structure of a pulp fiber, rather, these modified cellulosic materials are typically granular or have a regenerated fibril form.

A need exists for a highly absorbent material suitable for use in personal care absorbent products, the absorbent material having absorptive properties similar to synthetic, highly absorptive materials and at the same time offering the advantages of liquid wicking and distribution associated with fluff pulp fibers. Accordingly, there is a need for a fibrous superabsorbent that combines the advantageous liquid storage capacity of superabsorbent polymers and the advantageous liquid wicking of fluff pulp fibers. Ideally, the fibrous superabsorbent is economically viable for use in personal care absorbent products and is biodegradable thereby making the disposal of used absorbent products environmentally friendly. The present invention seeks to fulfill these needs and provides further related advantages.

SUMMARY OF THE INVENTION

In one aspect, the present invention provides crosslinked, carboxyalkyl cellulose fibers are provided. The fibers of the invention are substantially water-insoluble, water-swellable, non-regenerated, carboxyalkyl cellulose fibers having a surface having the appearance of the surface of a cellulose fiber. The fibers of the invention include a plurality of non-permanent intra-fiber metal crosslinks and a plurality of permanent intra-fiber crosslinks.

The non-permanent intra-fiber metal crosslinks include multi-valent metal ion crosslinks. The multi-valent metal ion crosslinks include one or more metal ions selected from aluminum, boron, bismuth, titanium, zirconium, cerium, and chromium ions, and mixtures thereof.

The permanent intra-fiber crosslinks include covalent crosslinks with an organic compound having at least two functional groups capable of reacting with at least one functional group selected from carboxyl, carboxylic acid, and hydroxyl groups. In one embodiment, the organic compound is a dihalide that provides a diether crosslink. In another embodiment, the organic compound is a polycarboxylic acid that provides a diester crosslink.

In one embodiment, the invention provides substantially water-insoluble, water-swellable, non-regenerated, carboxyalkyl cellulose fibers, wherein the fibers have a surface having the appearance of the surface of a cellulose fiber, and wherein the fibers comprise a plurality of non-permanent intra-fiber metal crosslinks and a plurality of permanent intra-fiber crosslinks, wherein the permanent intra-fiber crosslinks comprise covalent crosslinks formed from treatment with 1,3-dichloro-2-propanol.

In another aspect of the invention, fiber bundles are provided. The fiber bundle includes a plurality of substantially water-insoluble, water-swellable, non-regenerated, carboxyalkyl cellulose fibers having a surface having the appearance of the surface of a cellulose fiber. The fibers include a plurality of non-permanent intra-fiber metal crosslinks and a plurality of permanent intra-fiber crosslinks. The non-permanent intra-fiber metal crosslinks include multi-valent metal ion crosslinks. The multi-valent metal ion crosslinks include one or more metal ions selected from aluminum, boron, bismuth, titanium, zirconium, cerium, and chromium ions, and mixtures thereof.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

The present invention provides substantially water-insoluble, water-swellable, crosslinked carboxyalkyl cellulose fibers; and substantially water-insoluble, water-swellable, crosslinked carboxyalkyl cellulose fiber bundles. Methods for making the substantially water-insoluble, water-swellable fibers and fiber bundles are described.

Figure 1A:
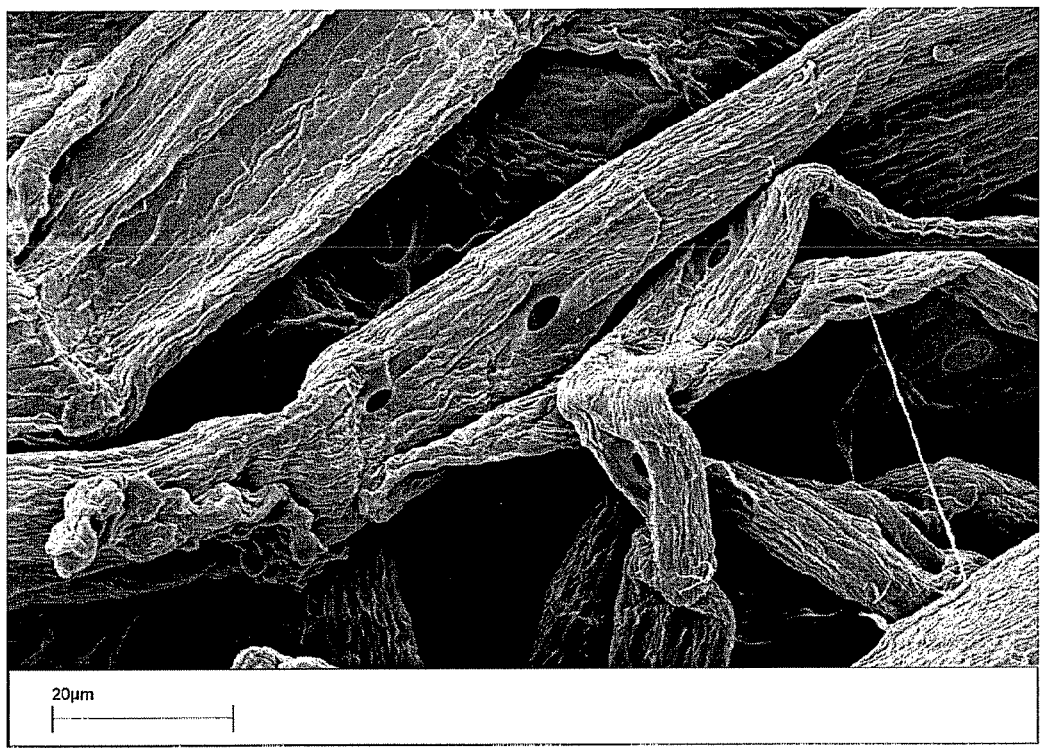
FIG. 1A is a scanning electron microscope photograph (1000×) of cellulose fibers useful for making the representative crosslinked carboxymethyl cellulose fibers of the invention.
Figure 1B:
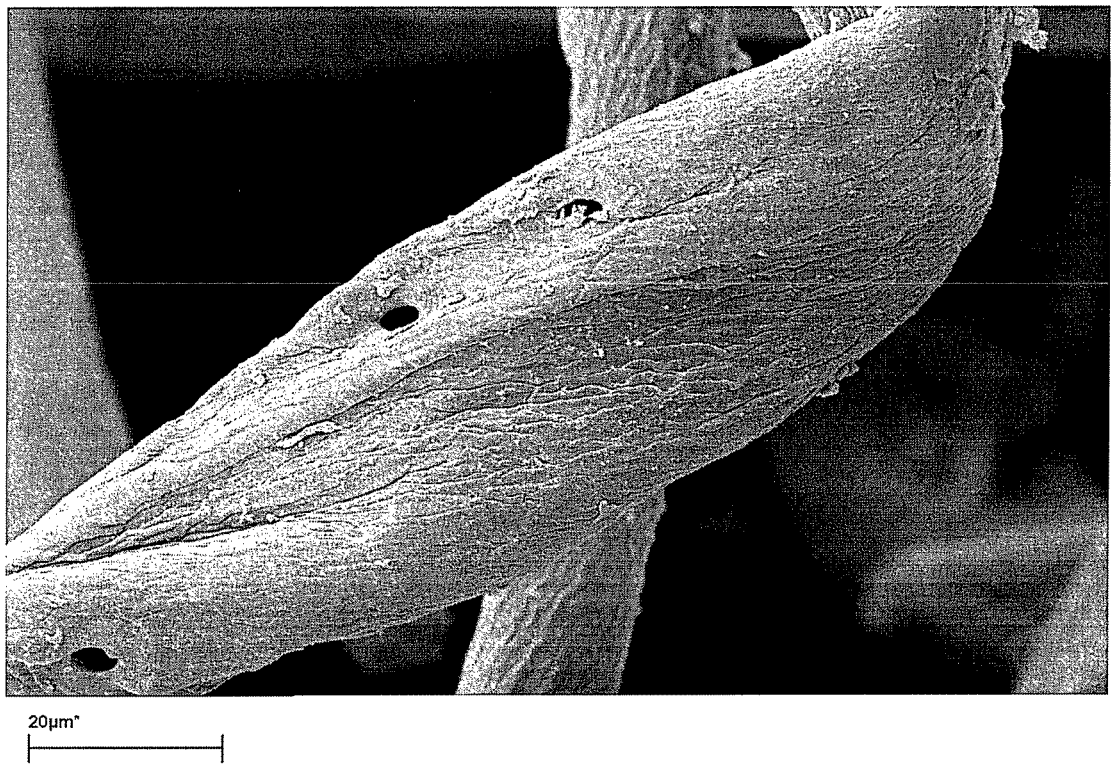
FIG. 1B is a scanning electron microscope photograph (1000×) of representative crosslinked carboxymethyl cellulose fibers of the invention.
Figure 2:
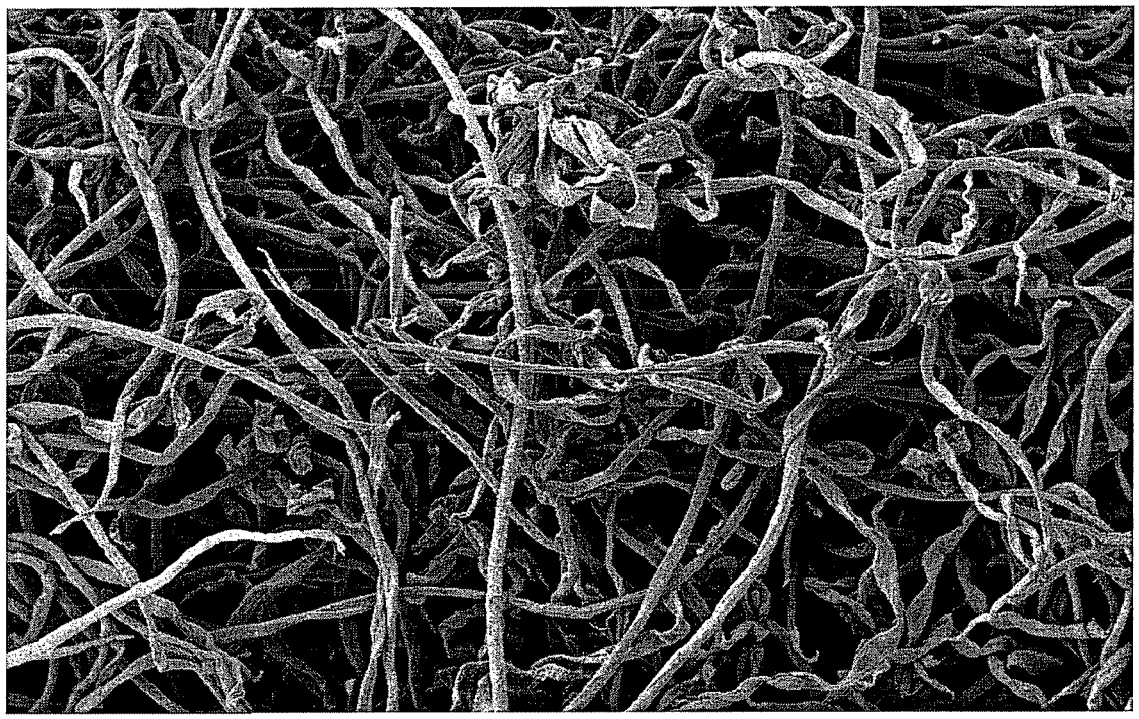
FIG. 2 is a scanning electron microscope photograph (50×) of representative crosslinked carboxymethyl cellulose fibers of the invention.

In one aspect, the present invention provides substantially water-insoluble, water-swellable, non-regenerated, carboxyalkyl cellulose fibers. The fibers have a surface having the appearance of the surface of a cellulose fiber and include a plurality of non-permanent intra-fiber metal crosslinks and a plurality of permanent intra-fiber metal crosslinks. As can be seen in FIGS. 1B and 2, the fibers of the invention have irregular surface patterns (including striations, pits, and pores) coextensive with the fibers' surface. The carboxyalkyl cellulose fibers of the invention are fibers having superabsorbent properties. The fibers are water-swellable, water-insoluble fibers that substantially retain a fibrous structure in their expanded, water-swelled state.

The fibers of the invention are cellulosic fibers that have been modified by carboxyalkylation and crosslinking. Water swellability is imparted to the fibers through carboxyalkylation and crosslinking renders the fibers substantially insoluble in water. The fibers have a degree of carboxyl group substitution effective to provide advantageous water swellability. The fibers are crosslinked to an extent sufficient to render the fiber water insoluble. The fibers have a liquid absorption capacity that is increased compared to unmodified fluff pulp fibers.

The fibers are substantially insoluble in water. As used herein, fibers are considered to be water soluble when they substantially dissolve in excess water to form a solution, losing their fiber form and becoming essentially evenly dispersed throughout the water solution. Sufficiently carboxyalkylated cellulosic fibers that are free from a substantial degree of crosslinking will be water soluble, whereas the fibers of the invention, carboxyalkylated and crosslinked fibers, are substantially water insoluble.

The fibers of the invention are substantially water-insoluble, water-swellable fibers. As used herein, the term "substantially water-insoluble, water-swellable" refers to fibers that, when exposed to an excess of an aqueous medium (e.g., bodily fluids such as urine or blood, water, synthetic urine, or 0.9 weight percent solution of sodium chloride in water), swell to an equilibrium volume, but do not dissolve into solution.

Figure 1C:
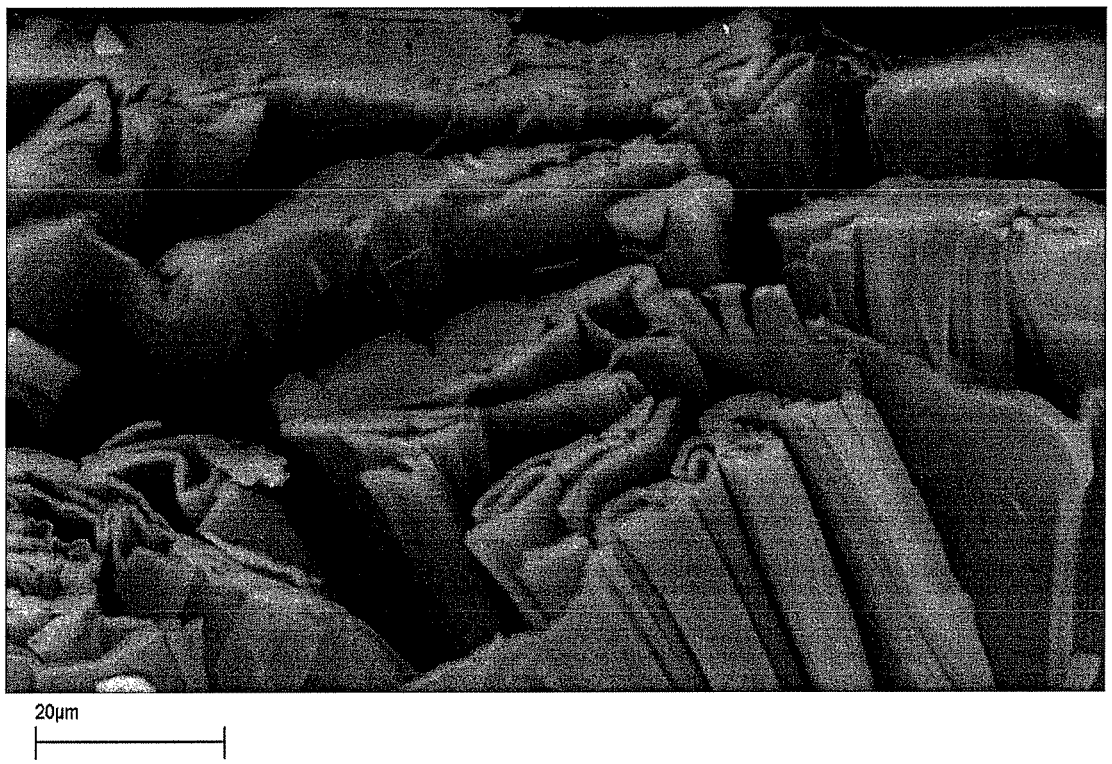
FIG. 1C is a scanning electron microscope photograph (1000×) of regenerated cellulose fibers.

The water-swellable, water-insoluble fibers of the invention have a surface having the appearance of the surface of a cellulose fiber. Like native fibers, the fibers have a surface that includes striations, pits, and pores. The fibers of the invention retain the surface structure of cellulose fibers because the fibers of the invention are prepared by methods that do not include dissolving the fibers into solution and then regenerating those fibers from the solution. Fibers that are prepared by regeneration from solution substantially lack typical fiber structures present in native fibers. Regenerated fibers lack, among other structural features, surface structure (e.g., striations, pits, and pores). FIGS. 1A, 1B, and 1C are photomicrographs comparing the surfaces of representative wood pulp fibers, representative fibers of the invention (prepared from the wood pulp fibers shown in FIG. 1A), and representative regenerated fibers, respectively. Referring to FIGS. 1A and 1B, the surfaces of representative wood pulp fibers and representative fibers of the invention are shown to include features (e.g., irregular surface patterns coextensive with the fibers' surface). In contrast, the surface of representative regenerated fibers substantially lack such surface structure (see FIG. 1C).

As used herein, the term "regenerated fiber" refers to a fiber that has been prepared by regeneration (i.e., return to solid form) from a solution that includes dissolved fiber. The term "non-regenerated" refers to a fiber that has not been dissolved into solution and then regenerated (i.e., returned to solid form) from that solution. As noted above, whereas the non-regenerated fibers of the invention substantially retain the surface structure of the cellulose fibers from which they are made, regenerated fibers do not.

The fibers of the invention include non-permanent intra-fiber crosslinks. The non-permanent intra-fiber crosslink is a metal-cellulose crosslink formed using a multi-valent metal ion. The non-permanent crosslinks can unform and reform in use (e.g., dissociate and re-associate on liquid insult in a personal care absorbent product). The fibers of the invention further include permanent intra-fiber crosslinks. Permanent intra-fiber crosslinks are stable in use and do not dissociate and re-associate on liquid insult in a personal care absorbent product.

The fibers of the invention are substantially insoluble in water while being capable of absorbing water. The fibers of the invention are rendered water insoluble by virtue of a plurality of intra-fiber crosslinks.

As used herein, the term "non-permanent intra-fiber metal crosslinks" refers to the nature of the crosslinking that occurs within individual fibers of the invention (i.e., intra-fiber) and among and between each fiber's constituent cellulose polymers.

The fibers of the invention are intra-fiber crosslinked with a metal crosslink. The metal crosslink arises as a consequence of an associative interaction (e.g., bonding) between functional groups on the fiber's cellulose polymers (e.g., carboxy, carboxylate, or hydroxyl groups) and a multi-valent metal species. Suitable multi-valent metal species include metal ions having a valency of two or greater and that are capable of forming an associative interaction with a cellulose polymer (e.g., reactive toward associative interaction with the polymer's carboxy, carboxylate, or hydroxyl groups). The cellulose polymers are crosslinked when the multi-valent metal species forms an associative interaction with functional groups on the cellulose polymer. A crosslink may be formed within a cellulose polymer or may be formed between two or more cellulose polymers within a fiber. The extent of crosslinking affects the water solubility of the fibers and the ability of the fiber to swell on contact with an aqueous liquid (i.e., the greater the crosslinking, the greater the insolubility).

The fibers of the invention include non-permanent intra-fiber metal crosslinks. As used herein, the term "non-permanent" refers to the metal-cellulose crosslink. Crosslinked cellulose fibers are well known and it is generally understood that the crosslinks of such fibers are generally permanent in nature (i.e., crosslinks that are stable to ordinary use conditions, such as cellulose wetting on liquid insult occurring in a personal care absorbent product). Permanent crosslinks are those that do not dissociate during the fibers' use and are typically covalent crosslinks derived from reaction of an organic compound having at least two functional groups capable of reacting with at least one functional group of a cellulose polymer (e.g., a diether crosslink derived from crosslinking cellulose with a dihalide such as 1,3-dichloro-2-propanol, or a diester crosslink derived from crosslinking cellulose with citric acid). A non-permanent crosslink is a crosslink that provides a crosslink within or between a fiber's cellulose polymers, but is reactive toward liquid insult. The non-permanent crosslinks of the fibers of the present invention can be unformed and reformed on liquid insult. The metal crosslinks of the fibers of the invention have the characteristic of dissociation on liquid insult, which allow the fibers to expand and swell during liquid acquisition. Once liquid acquisition is complete (i.e., insult terminated), re-association between the dissociated multi-valent metal ion species and the cellulose polymer occurs to re-establish a crosslink. In such an instance, the new crosslink is formed in fibers now swollen with acquired liquid. It will be appreciated that the process of dissociating and re-associating (breaking and reforming crosslinks) the multi-valent metal ion and cellulose polymer is dynamic and also occurs during liquid acquisition. By virtue of the non-permanent crosslinks, the fibers of the invention have the unique property of maintaining structural integrity while swelling on liquid insult.

The fibers of the invention include non-permanent intra-fiber metal crosslinks. The metal crosslinks include multi-valent metal ion crosslinks that include one or more metal ions selected from aluminum, boron, bismuth, cerium, chromium, titanium, zirconium, and mixtures thereof. In one embodiment, the crosslinks are formed through the use of an aluminum crosslinking agent. Suitable aluminum crosslinking agents include aluminum acetates, aluminum sulfate, aluminum chloride, and aluminum lactate. Representative aluminum acetates include aluminum monoacetate, aluminum diacetate, aluminum triacetate, aluminum hemiacetate, aluminum subacetate, and mixtures of aluminum acetates made from non-stoichiometric amounts of acetate and hydroxide in an organic solvent that is water miscible. In one embodiment, the aluminum crosslinking agent is aluminum monoacetate stabilized with boric acid (aluminum acetate, basic, containing boric acid as stabilizer, $CH_3CO_2Al(OH)_2 \cdot \frac{1}{3}H_3BO_3$, Aldrich Chemical Co.). In another embodiment, the aluminum crosslinking agent is prepared immediately prior to use (see Examples 4 and 5).

The fibers of the invention include non-permanent metal ion intra-fiber crosslinks and permanent intra-fiber crosslinks. Permanent intra-fiber crosslinks are crosslinks that are stable in use (e.g., stable to liquid insult when in use in a personal care absorbent product, such as an infant diaper). Permanent intra-fiber crosslinks can be made by crosslinking the fibers with an organic compound having at least two functional groups capable of reacting with at least one functional group selected from the group consisting of carboxyl, carboxylic acid, and hydroxyl groups. Permanent intra-fiber crosslinks include ether and ester crosslinks (e.g., diether crosslinks).

Permanent crosslinks can be incorporated into the fibers of the invention in several ways: prior to carboxyalkylation; at the same time as carboxyalkylation; after carboxyalkylation and before treating with a multi-valent metal ion crosslinking agent; or after treating with a multi-valent metal ion crosslinking agent.

In one embodiment, crosslinked carboxyalkyl cellulose fibers of the invention can be made from crosslinked pulp fibers. The crosslinks of the crosslinked cellulose fibers useful in making the carboxyalkyl cellulose are crosslinks that are stable (i.e., permanent) to the carboxyalkylation reaction conditions. A method for making crosslinked carboxyalkyl cellulose fibers from crosslinked fibers and subsequent crosslinking to incorporate non-permanent crosslinks is described in Example 6. Example 6 describes aluminum acetate crosslinked carboxyalkyl cellulose made from 1,3-dichloro-2-propanol crosslinked fibers and aluminum acetate crosslinked carboxyalkyl cellulose made from glycerol diglycidal crosslinked fibers.

In one embodiment, crosslinked carboxyalkyl cellulose fibers of the invention can be made by treating cellulose fibers with a crosslinking agent that provides permanent crosslinks and a carboxyalkylating agent during carboxyalkylation. A method for making crosslinked carboxyalkyl cellulose fibers by treating fibers with a crosslinking agent and a carboxyalkylating agent during carboxyalkylation and subsequent crosslinking to incorporate non-permanent crosslinks is described in Example 7. Example 7 describes treating cellulose fibers with 1,3-dichloro-2-propanol and sodium monochloroacetate to provide carboxymethyl cellulose having permanent crosslinks followed by crosslinking with aluminum chloride to incorporate non-permanent crosslinks.

Suitable crosslinking agents useful in making ether crosslinks include dihalide crosslinking agents, such as 1,3-dichloro-2-propanol; diepoxide crosslinking agents, such as vinylcyclohexene dioxide, butadiene dioxide, and diglycidyl ethers (e.g., glycerol diglycidal, 1,4-butanediol diglycidal, and poly(ethylene glycol diglycidal)); sulfone compounds such as divinyl sulfone; bis(2-hydroxyethyl)sulfone, bis(2-chloroethyl)sulfone, and disodium tris($\beta$-sulfatoethyl)sulfonium inner salt; and diisocyanates.

Other suitable crosslinking agents useful for making permanent crosslinks include urea-based formaldehyde addition products (e.g., N-methylol compounds) and polycarboxylic acids.

Suitable urea-based crosslinking agents include methylolated ureas, methylolated cyclic ureas, methylolated lower alkyl substituted cyclic ureas, methylolated dihydroxy cyclic ureas, dihydroxy cyclic ureas, and lower alkyl substituted cyclic ureas. Specific preferred urea-based crosslinking agents include dimethylol urea (DMU, bis[N-hydroxymethyl]urea), dimethylolethylene urea (DMEU, 1,3-dihydroxymethyl-2-imidazolidinone), dimethyloldihydroxyethylene urea (DMDHEU, 1,3-dihydroxymethyl-4,5-dihydroxy-2-imidazolidinone), dimethylolpropylene urea (DMPU), dimethylolhydantoin (DMH), dimethyldihydroxy urea (DMDHU), dihydroxyethylene urea (DHEU, 4,5-dihydroxy-2-imidazolidinone), and dimethyldihydroxyethylene urea (DMeDHEU, 4,5-dihydroxy-1,3-dimethyl-2-imidazolidinone).

Polycarboxylic acid crosslinking agents include those described in U.S. Pat. Nos. 5,137,537; 5,183,707; and 5,190,563, describing the use of C2-C9 polycarboxylic acids that contain at least three carboxyl groups (e.g., citric acid and oxydisuccinic acid) as crosslinking agents. Suitable polycarboxylic acid crosslinking agents include citric acid, tartaric acid, malic acid, succinic acid, glutaric acid, citraconic acid, itaconic acid, tartrate monosuccinic acid, maleic acid, 1,2,3-propane tricarboxylic acid, 1,2,3,4-butanetetracarboxylic acid, all-cis-cyclopentane tetracarboxylic acid, tetrahydrofuran tetracarboxylic acid, 1,2,4,5-benzenetetracarboxylic acid, and benzenehexacarboxylic acid. Other polycarboxylic acids crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. Pat. No. 5,998,511.

Suitable crosslinking agents also include crosslinking agents that are reactive toward carboxylic acid groups. Representative organic crosslinking agents include diols and polyols, diamines and polyamines, diepoxides and polyepoxides, polyoxazoline functionalized polymers, and aminols having one or more amino groups and one or more hydroxy groups.

In some embodiments, mixtures and/or blends of crosslinking agents can also be used.

The crosslinking agent can include a catalyst to accelerate the bonding reaction between the crosslinking agent and cellulosic fiber. Suitable catalysts include acidic salts, such as ammonium chloride, ammonium sulfate, aluminum chloride, magnesium chloride, and alkali metal salts of phosphorous-containing acids.

The amount of crosslinking agent applied to the cellulosic fiber will depend on the particular crosslinking agent and is suitably in the range of from about 0.01 to about 10.0 percent by weight based on the total weight of cellulosic fiber. In one embodiment, the amount of crosslinking agent applied to the fibers is in the range from about 1.0 to about 8.0 percent by weight based on the total weight of fibers.

In one embodiment, the crosslinking agent can be applied to the cellulosic fibers as an aqueous alcoholic solution. Water is present in the solution in an amount sufficient swell the fiber to an extent to allow for crosslinking within the fiber's cell wall. However, the solution does not include enough water to dissolve the fiber. Suitable alcohols include those alcohols in which the crosslinking agent is soluble and the fiber to be crosslinked (i.e., unmodified or carboxyalkylated cellulosic fiber) is not. Representative alcohols include alcohols that include from 1 to 5 carbon atoms, for example, methanol, ethanol, n-propanol, isopropanol, n-butanol, isobutanol, s-butanol, and pentanols. In one embodiment, the alcohol is ethanol. In another embodiment, the alcohol is methanol.

It will be appreciated that due to their fibers' structure, the fibers of the invention can have a distribution of carboxyl and/or crosslinking groups along the fiber's length and through the fiber's cell wall. Generally, there can be greater carboxyalkylation and/or crosslinking on or near the fiber surface than at or near the fiber core. Surface crosslinking may be advantageous to improve fiber dryness and provide a better balance of total absorbent capacity and surface dryness. Fiber swelling and soak time can also effect the carboxyalkylation and crosslinking gradients. Such gradients may be due to the fiber structure and can be adjusted and optimized through control of carboxyalkylation and/or crosslinking reaction conditions.

The substantially water-insoluble, water-swellable, non-regenerated, carboxyalkyl cellulose fibers are absorbent fibers and may be used in a variety of applications. The fibers of the invention can be incorporated into personal care absorbent products (e.g., infant diapers, adult incontinence products, and feminine care products).

Cellulosic fibers are a starting material for preparing the fibers of the invention. Although available from other sources, suitable cellulosic fibers are derived primarily from wood pulp. Suitable wood pulp fibers for use with the invention can be obtained from well-known chemical processes such as the kraft and sulfite processes, with or without subsequent bleaching. Pulp fibers can also be processed by thermomechanical, chemithermomechanical methods, or combinations thereof. A high alpha cellulose pulp is also a suitable wood pulp fiber. The preferred pulp fiber is produced by chemical methods. Ground wood fibers, recycled or secondary wood pulp fibers, and bleached and unbleached wood pulp fibers can be used. Softwoods and hardwoods can be used. Suitable fibers are commercially available from a number of companies, including Weyerhaeuser Company. For example, suitable cellulosic fibers produced from southern pine that are usable with the present invention are available from Weyerhaeuser Company under the designations CF416, NF405, PL416, FR516, and NB416. Other suitable fibers include northern softwood and eucalyptus fibers. Suitable non-wood fibers include rye grass fibers and cotton linters.

Cellulosic fibers having a wide range of degree of polymerization are suitable for forming the fiber of the invention. In one embodiment, the cellulosic fiber has a relatively high degree of polymerization, greater than about 1000, and in another embodiment, about 1500 to about 2500.

In one embodiment, the fibers have an average length greater than about 1.0 mm. Consequently, the fibers are suitably prepared from fibers having lengths greater than about 1.0 mm. Fibers having lengths suitable for preparing the fibers include southern pine, northern softwood, and eucalyptus fibers, the average length of which is about 2.8 mm, about 2.0 mm, and about 1.0 mm, respectively.

The fibers of the invention are carboxyalkylated cellulosic fibers. As used herein, "carboxyalkylated cellulosic fibers" refer to cellulosic fibers that have been carboxyalkylated by reaction of cellulosic fibers with a carboxyalkylating agent. It will be appreciated that the term "carboxyalkylated cellulosic fibers" include free acid and salt forms of the carboxyalkylated fibers. Suitable metal salts include sodium, potassium, and lithium salt, among others. Carboxyalkylated cellulosic fibers can be produced by reacting a hydroxyl group of the cellulosic fiber with a carboxyalkylating agent to provide a carboxyalkyl cellulose.

Suitable carboxyalkylating agents include monochloroacetic acid and its salts, 3-chloropropionic acid and its salts, and acrylamide. The carboxyalkyl celluloses useful in preparing the fibers of the invention include carboxymethyl celluloses and carboxyethyl celluloses.

The fibers of the invention can be characterized as having an average degree of carboxyl group substitution of from about 0.5 to about 1.5. In one embodiment, the fibers have an average degree of carboxyl group substitution of from about 0.8 to about 1.2. In another embodiment, the fibers have an average degree of carboxyl group substitution of about 1.0. As used herein, the "average degree of carboxyl group substitution" refers to the average number of moles of carboxyl groups per mole of glucose unit in the fiber. It will be appreciated that the fibers of the present invention include a distribution of carboxyl fibers having an average degree of carboxyl substitution as noted above.

As noted above, the fibers of the invention are highly absorptive.

The fibers of the invention have a liquid absorbent capacity of from about 8 to about 40 g/g as measured by the centrifuge retention capacity (CRC) test described below. In one embodiment, the fibers have a capacity of at least about 20 g/g. In another embodiment, the fibers have a capacity of at least about 25 g/g.

The fibers of the invention have a liquid absorbent capacity of from about 30 to about 70 g/g as measured by the free swell capacity test described below. In one embodiment, the fibers have a capacity of at least about 50 g/g. In another embodiment, the fibers have a capacity of at least about 60 g/g.

The fibers of the invention have a liquid absorbent capacity of from about 10 to about 40 g/g as measured by the absorbency under load (AUL) test described below. In one embodiment, the fibers have a capacity of at least about 20 g/g. In another embodiment, the fibers have a capacity of at least about 30 g/g.

The fibers of the invention can be formed into pads by, for example, conventional air-laying techniques and the performance characteristics of those pads determined. An advantageous property of the fibers of the invention is that pads formed from these fibers demonstrate rapid liquid acquisition times for multiple insults. For certain pads subjected to multiple insults, liquid acquisition times for subsequent insults actually decreases. The liquid acquisition times for subsequent insults for pads made from fibers of the invention are measured by the fluid intake flowback evaluation (FIFE) described below. The FIFE results for pads formed from the fibers of the invention are presented in Example 3.

In addition to advantageous liquid acquisition, pads formed from the fibers of the invention demonstrate significant strength and integrity after being subject to multiple insults. Pad wet strength results for pads formed from the fibers of the invention are presented in Example 3.

Methods for making the fibers of the invention are described in Examples 3, 6, and 7. The absorbent properties of the fibers are also summarized in these examples.

In another aspect of the invention, fiber bundles are provided. The fiber bundles are an aggregate (or plurality) of the fibers of the invention described above. In the fiber bundles, adjacent fibers are in contact with each other. The bundle is an aggregate of the fibers in which contact between adjacent fibers is maintained mechanically by, for example, friction or entanglement; or chemically by, for example, hydrogen bonding or crosslinking.

The fiber bundle can have a diameter of from about 50 to about 2000 µm, a basis weight of from about 200 to about 2000 g/m$^2$, and a density of from about 0.03 to about 1.5 g/cm$^3$.

Like their component fibers, the fiber bundles of the invention exhibit significant absorbent capacity.

The fibers of the invention can be prepared by a method that includes carboxylating and crosslinking cellulose fibers. In one embodiment, cellulosic fibers are carboxyalkylated and then crosslinked. In this method, carboxyalkylated cellulosic fibers are treated with an amount of crosslinking agent sufficient to render the resulting fibers substantially insoluble in water. In another embodiment, cellulosic fibers are crosslinked then carboxyalkylated. In this method, crosslinked cellulosic fibers are carboxyalkylated to render the resulting fibers highly water absorptive. The fibers formed by either method are highly water absorptive, water swellable, and water insoluble.

The method includes carboxyalkylating cellulose fibers by treating cellulose fibers with a carboxyalkylating agent and a crosslinking agent or agents. In the method, the carboxyalkyl cellulose fibers are not dissolved and therefore retain their fibrous form throughout the method steps.

In one embodiment, the method further includes drying the substantially water-insoluble, water-swellable, carboxyalkyl cellulose fibers.

In one embodiment, the substantially water-insoluble, water-swellable, carboxyalkyl cellulose fibers are fiberized to provide individualized fibers. In another embodiment, the substantially water-insoluble, water-swellable, carboxyalkyl cellulose fibers are fiberized to provide fiber bundles comprising substantially water-insoluble, water-swellable, carboxyalkyl cellulose fibers.

The carboxyalkylating agent can be monochloroacetic acid or its salts, 3-chloropropionic acid or its salts, or acrylamide.

The carboxyalkylating medium comprises a mixture of one or more alcohols and water. In one embodiment, the alcohol is ethanol. In another embodiment, the alcohol is isopropanol.

The fibers of the invention include non-permanent intra-fiber crosslinks formed through the use of multi-valent metal ion crosslinking agents. These crosslinking agents include a metal ion selected from aluminum, boron, bismuth, titanium, zirconium, cerium, or chromium ions. Mixtures can also be used. The multi-valent metal ion crosslinking agent is applied in an amount from about 0.1 to about 10 percent by weight based on the weight of fibers. The amount of crosslinking agent will depend on the nature of the crosslinking agent and the desired absorbent properties in the product fiber.

In one embodiment, the multi-valent metal ion crosslinking agent is an aluminum compound. Suitable aluminum crosslinking agents include aluminum acetates, aluminum sulfate, aluminum chloride, and aluminum lactate. Representative aluminum acetates include aluminum monoacetate, aluminum diacetate, aluminum triacetate, aluminum hemiacetate, aluminum subacetate, and mixtures of aluminum acetates made from non-stoichiometric amounts of acetate and hydroxide in an organic solvent that is water miscible. In one embodiment, the aluminum crosslinking agent is aluminum monoacetate stabilized with boric acid (aluminum acetate, basic, containing boric acid as stabilizer, $CH_3CO_2Al(OH)_2 \cdot \frac{1}{3}H_3BO_3$, Aldrich Chemical Co.). In another embodiment, the aluminum crosslinking agent is prepared immediately prior to use.

As noted above, in addition to non-permanent metal ion crosslinks, the fibers of the invention also include permanent intra-fiber crosslinks. Permanent intra-fiber crosslinks can be made by crosslinking the fibers with an organic compound having at least two functional groups capable of reacting with at least one functional group selected from the group consisting of carboxyl, carboxylic acid, and hydroxyl groups. Suitable crosslinking agents for making permanent crosslinks are described above. Representative permanent crosslinks include ether and ester crosslinks.

The permanent crosslinks can be incorporated into the fibers prior to, during, or after carboxyalkylation.

In one embodiment, the method includes treating the cellulose fibers with a crosslinking agent prior to carboxyalkylating the cellulose fibers. In this method, crosslinked cellulose fibers are carboxyalkylated. In this embodiment, the carboxyalkylated cellulose fibers made from crosslinked fibers are subsequently treated with a multi-valent metal ion crosslinking agent to impart non-permanent crosslinks to the fibers.

In one embodiment, the method includes treating the cellulose fibers with a crosslinking agent at the same time as carboxyalkylating the cellulose fibers. In this method, cellulose fibers are crosslinked during carboxylation. In this embodiment, the carboxyalkylated, crosslinked cellulose fibers are subsequently treated with a multi-valent metal ion crosslinking agent to impart non-permanent crosslinks to the fibers.

In one embodiment, the method includes treating the fibers with a crosslinking agent after carboxyalkylating the cellulose fibers and prior to treating the carboxyalkyl cellulose fibers with a multi-valent metal ion crosslinking agent.

In another embodiment, the method further includes treating the fibers with a crosslinking agent after treating the carboxyalkyl cellulose fibers with a multi-valent metal ion crosslinking agent.

The multi-valent metal ion crosslinking agent is applied to the fibers in an amount from about 0.1 to about 10 percent by weight based on the weight of fibers and the crosslinking agent for making permanent crosslinks (e.g., organic compound) is applied to the fibers in an amount from about 0.1 to about 5 percent by weight based on the weight of fibers. In one embodiment, the multi-valent metal ion crosslinking agent is applied in an amount from about 1 to about 8 percent by weight based on the weight of fibers and the crosslinking agent for making permanent crosslinks is applied in an amount from about 0.5 to about 2 percent by weight based on the weight of fibers.

Figure 3:
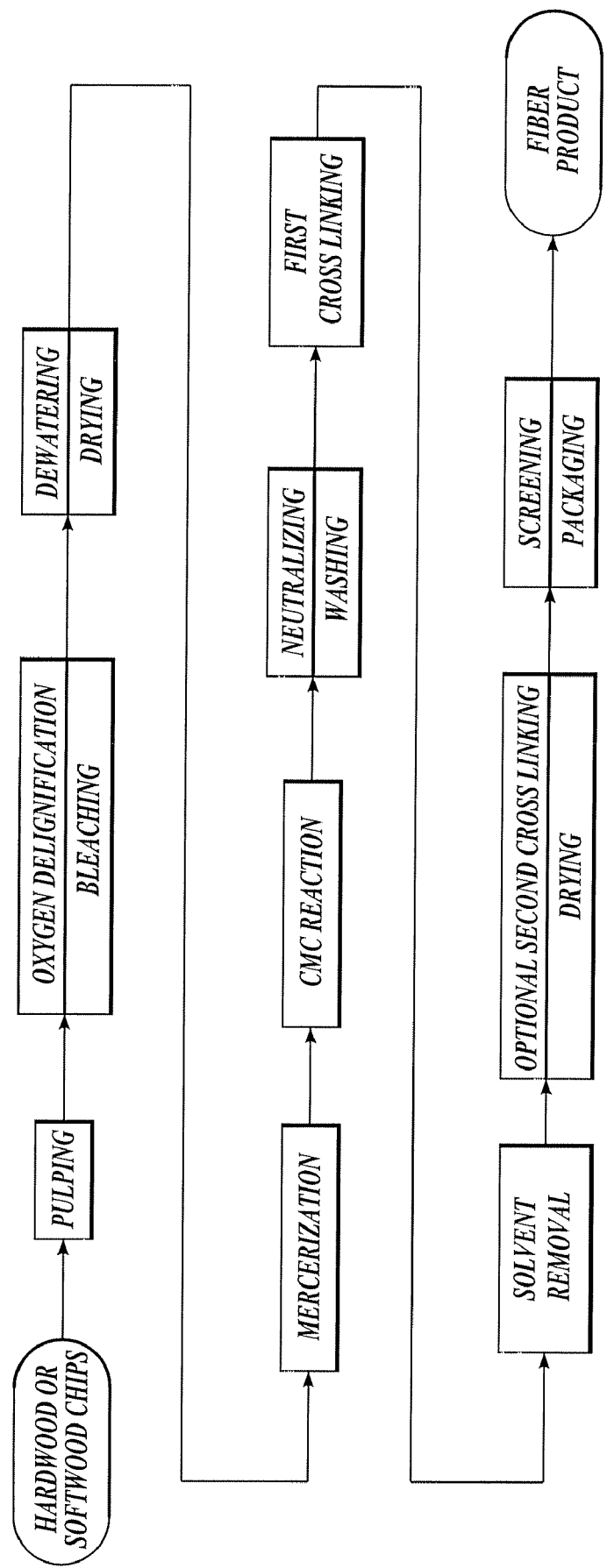
FIG. 3 is a flow chart illustrating a representative method of the invention for making crosslinked carboxymethyl cellulose fibers and crosslinked carboxymethyl cellulose fiber bundles.

A schematic diagram illustrating one representative method for making substantially water-insoluble, water-swellable, crosslinked carboxyalkyl cellulose fibers and fiber bundles is illustrated in FIG. 3. The following is a description of one representative method for making the fibers and fiber bundles.

Pulp Preparation

Wood pulp fibers are the starting material for the preparation of the fibers and fiber bundles of the present invention. In a representative method, hardwood or softwood chips are cooked in a conventional or modified continuous digester to provide pulp having a Kappa number between 20 and 40. The kraft pulp can then be delignified in an oxygen delignification reactor and then subsequently partially or fully bleached by conventional bleaching processes (e.g., elemental chlorine-free bleaching) and bleaching sequences (DEopD or DEopDED). The pulp capillary viscosity produced by the pulping, delignification, and bleaching steps is greater than about 25 cps and the pulp has a brightness of up to about 87% ISO. The bleached pulp at a consistency of from about 10 to 15% is then dewatered (e.g., press or centrifuge) to provide pulp at a consistency of 30-35%. The dewatered pulp is then further dried to a consistency of 50-60% (i.e., never-dry dried pulp) or 85-90% (air-dried pulp) by, for example, a through-air dryer. The dry pulp is then ready for carboxyalkyl cellulose formation.

Carboxyalkyl Cellulose Preparation

High consistency pulp (e.g., 50-90%) is introduced into either a batch or a continuous carboxyalkyl cellulose reactor at about room temperature under nitrogen. The pulp fibers are then treated with 50% by weight sodium hydroxide in water (i.e., mercerization) at about 25 degrees for 0.5 to 1 hour. The alkalized pulp is then treated with a carboxyalkylation agent in alcohol (e.g., 50% by weight monochloroacetic acid in ethanol) at a temperature of between about 55-75° C. for three to four hours. During this time the consistency of pulp in the reactor is from about 15 to about 25% with the ratio of alcohol solvent to water less than about 2. Once the carboxyalkylation (i.e., etherization) is complete, the carboxyalkyl cellulose fibers are neutralized by the addition of acid (e.g., 33% by weight hydrogen chloride in water).

In the process, the carboxyalkyl cellulose (e.g., carboxymethyl cellulose, CMC) is produced, having a degree of substitution (DS) of from about 0.5 to about 1.5. The degree of substitution is defined as the moles of carboxyl groups introduced to the fiber per mol of anhydroglucose units. In a continuous process, the alkylization and etherification chemicals are mixed with the pulp in a mixer and the mixture is transported to the reactor without stirring. For a batch process, the chemicals are mixed with the pulp in the reactor with continuous stirring.

As noted above, the carboxyalkyl cellulose preparation includes three stages: (1) alkylization (i.e., mercerization); (2) carboxyalkylation (i.e., etherification); and (3) neutralization and washing.

Representative process conditions for the alkylization stage include a temperature from about 0 to 30° C., a time of about 0.5 to 1.5 hour, a liquor (i.e., alcohol solvent and water) to pulp ratio of from about 2 to about 50, a solvent (ethanol or isopropanol) to water ratio of about 1 to about 10, and a sodium hydroxide charge rate of about 2-4 mol/mol cellulose.

Representative process parameters for the carboxyalkylation reaction stage include a temperature of from about 50 to about 80° C., a process time of from about 2 to about 4 hours, a liquor to pulp ratio of from about 2 to about 20, a solvent to water ratio of from about 1 to about 25, and a carboxyalkylating agent (monochloroacetic acid) charge rate of about 1 to 2 mol/mol cellulose.

After neutralization, the carboxyalkylated cellulose fibers are washed (e.g., belt washer or centrifuge) with a mixture of an alcohol (e.g., ethanol) and water (concentration 60-80% mass). In the process, residual salt is less than 5% mass. During the washing step, acetic acid is used to neutralize the carboxyalkyl cellulose fibers.

The carboxyalkyl cellulose fibers so produced are ready for crosslinking.

Crosslinked Carboxyalkyl Cellulose Fiber Preparation

Carboxyalkyl cellulose fibers from the carboxyalkylation reactor are introduced to a continuous reactor at a consistency of about 30%. In the reactor, the carboxyalkyl cellulose fibers are treated with a crosslinking agent at a consistency of about 5-25% at a temperature of from about 20 to about 75° C., and for a time of from 0.2 to 2 hours. The temperature and time may depend on the nature of the crosslinking agent. In a representative crosslinking reactor, the liquor (i.e., organic solvent and water) to pulp ratio is from about 2 to 20, the organic solvent to water ratio is from about 1 to about 2, and the crosslinking agent charge rate is from about 2 to about 7% mass based on the weight of carboxyalkyl cellulose fibers.

In one embodiment, a crosslinking (permanent crosslinking) reaction is carried out in the carboxyalkyl cellulose reactor where crosslinking (permanent) occurs substantially simultaneously with carboxyalkylation. Crosslinked carboxyalkyl cellulose fibers (having permanent crosslinks) leaving the crosslinking reactor are then subject to solvent removal (e.g., through the use of steam by a steam stripper) to provide substantially solvent-free crosslinked carboxyalkyl cellulose fibers. When the crosslinking agent is applied to the carboxyalkyl cellulose fibers in ethanol, the ethanol stripped from the crosslinked fibers can be returned to an ethanol distillation column for ethanol recovery and recycling.

Ethanol for solvent in the carboxyalkylation reaction can be fed from an ethanol storage tank in liquid communication with an ethanol distillation column for receiving and recycling ethanol from other steps in the process.

Ethanol for the crosslinking step as a solvent for the crosslinking agent can be fed to the crosslinking reactor from ethanol storage.

The substantially ethanol-free fibers can be further defiberized in a fluffer (e.g., pin fluffer or shredder) to provide crosslinked carboxyalkyl cellulose fibers and related crosslinked carboxyalkylated cellulose fiber bundles.

Further Crosslinking of Crosslinked Carboxyalkyl Cellulose Fibers

The substantially ethanol-free crosslinked carboxyalkylated cellulose fibers may be optionally further crosslinked by applying a second crosslinking agent to the crosslinked carboxyalkylated cellulose fibers and then drying the treated crosslinked carboxyalkylated cellulose fibers to provide crosslinked carboxyalkylated cellulose fibers. The optional additional crosslinking occurs during drying, which can be carried out using, for example, fluidized bed dryer, flash dryer, belt conveyor dryer, or drum dryer.

Screening and Packaging Crosslinked Carboxyalkyl Cellulose Fibers

The dried crosslinked carboxyalkyl cellulose fibers and/or fiber bundles can be screened to select particular size distributions. The final fiber and/or fiber bundle product can be sheeted by air-laying processes and the final product packaged in rolls. Alternatively, the fiber and/or fiber bundle products can be baled.

Solvent Recovery Salt Recovery and Waste Treatment

The filtrate from the carboxyalkyl cellulose reactor wash and the off gases from the stripper and dryer can be sent to a solvent recovery process. Solvent (e.g., ethanol) can be recovered from the filtrate using a distillation device. Solvent recovered can be recycled to the process. The distillation device residue can be sent to salt recovery process. Residual filtrate can be sent to waste treatment.

The absorbent properties of the crosslinked carboxyalkyl cellulose fibers and fiber bundles can be determined directly or by forming the fibers and/or bundles into pads by air-laying techniques and then testing the pad performance.

Test Methods

Free Swell and Centrifuge Retention Capacities

The materials, procedure, and calculations to determine free swell capacity (g/g) and centrifuge retention capacity (CRC) (g/g) were as follows.

Test Materials:

Japanese pre-made empty tea bags (available from Drugstore.com, IN PURSUIT OF TEA polyester tea bags 93 mm×70 mm with fold-over flap) (http:www.mesh.ne.jp/tokiwa/).

Balance (4 decimal place accuracy, 0.0001 g for air-dried superabsorbent polymer (ADS SAP) and tea bag weights); timer; 1% saline; drip rack with clips (NLM 211); and lab centrifuge (NLM 211, Spin-X spin extractor, model 776S, 3,300 RPM, 120 v).

Test Procedure:

1. Determine solids content of ADS.
2. Pre-weigh tea bags to nearest 0.0001 g and record.
3. Accurately weigh 0.2025 g+/−0.0025 g of test material (SAP), record and place into pre-weighed tea bag (air-dried (AD) bag weight). (ADS weight+AD bag weight=total dry weight).
4. Fold tea bag edge over closing bag.
5. Fill a container (at least 3 inches deep) with at least 2 inches with 1% saline.
6. Hold tea bag (with test sample) flat and shake to distribute test material evenly through bag.
7. Lay tea bag onto surface of saline and start timer.
8. Soak bags for specified time (e.g., 30 minutes).
9. Remove tea bags carefully, being careful not to spill any contents from bags, hang from a clip on drip rack for 3 minutes.
10. Carefully remove each bag, weigh, and record (drip weight).
11. Place tea bags onto centrifuge walls, being careful not to let them touch and careful to balance evenly around wall.
12. Lock down lid and start timer. Spin for 75 seconds.
13. Unlock lid and remove bags. Weigh each bag and record weight (centrifuge weight).

Calculations:

The tea bag material has an absorbency determined as follows:

Free Swell Capacity, factor=5.78
Centrifuge Capacity, factor=0.50

$Z$=Oven dry SAP wt (g)/Air dry SAP wt (g)

Free Capacity (g/g):

$$\frac{[(\text{drip } wt(g) - \text{dry bag } wt(g)) - (AD\ SAP\ wt(g))] -}{(AD\ SAP\ wt(g) * Z)}$$

Centrifuge Retention Capacity (g/g):

$$\frac{[(\text{centrifuge } wt(g) - \text{dry bag } wt(g) - (AD\ SAP\ wt(g))] -}{(AD\ SAP\ wt * Z)}$$

Absorbency Under Load (AUL)

The materials, procedure, and calculations to determine AUL were as follows.

Test Materials:

Mettler Toledo PB 3002 balance and BALANCE-LINK software or other compatible balance and software. Software set-up: record weight from balance every 30 sec (this will be a negative number. Software can place each value into EXCEL spreadsheet.

Kontes 90 mm ULTRA-WARE filter set up with fritted glass (coarse) filter plate. clamped to stand; 2 L glass bottle with outlet tube near bottom of bottle; rubber stopper with glass tube through the stopper that fits the bottle (air inlet); TYGON tubing; stainless steel rod/plexiglass plunger assembly (71 mm diameter); stainless steel weight with hole drill through to place over plunger (plunger and weight=867 g); VWR 9.0 cm filter papers (Qualitative 413 catalog number 28310-048) cut down to 80 mm size; double-stick SCOTCH tape; and 0.9% saline.

Test Procedure:

1. Level filter set-up with small level.
2. Adjust filter height or fluid level in bottle so that fritted glass filter and saline level in bottle are at same height.
3. Make sure that there are no kinks in tubing or air bubbles in tubing or under fritted glass filter plate.
4. Place filter paper into filter and place stainless steel weight onto filter paper.
5. Wait for 5-10 min while filter paper becomes fully wetted and reaches equilibrium with applied weight.
6. Zero balance.
7. While waiting for filter paper to reach equilibrium prepare plunger with double stick tape on bottom.
8. Place plunger (with tape) onto separate scale and zero scale.
9. Place plunger into dry test material so that a monolayer of material is stuck to the bottom by the double stick tape.
10. Weigh the plunger and test material on zeroed scale and record weight of dry test material (dry material weight 0.15 g+/−0.05 g).
11. Filter paper should be at equilibrium by now, zero scale.
12. Start balance recording software.
13. Remove weight and place plunger and test material into filter assembly.
14. Place weight onto plunger assembly.
15. Wait for test to complete (30 or 60 min)
16. Stop balance recording software.

Calculations:

A=balance reading (g)*−1 (weight of saline absorbed by test material)

B=dry weight of test material (this can be corrected for moisture by multiplying the AD weight by solids %).

AUL(g/g)=$A/B$(g 1% saline/1 g test material)

Saturated Retention Capacity

The saturated retention capacity is a measure of the total absorbent capacity of an absorbent garment, an absorbent structure, containment means and superabsorbent material, or a superabsorbent material. The saturated retention capacity is determined as follows. The material to be tested, having a moisture content of less than about 7 weight percent, is then weighed and submerged in an excess quantity of the room temperature (about 23° C.) 0.9% saline. The material is allowed to remain submerged for 20 minutes. After 20 minutes the material is removed from the urine and placed on a TEFLON coated fiberglass screen having 0.25 inch openings (commercially available from Taconic Plastics Inc. Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material. If material, such as superabsorbent material or fiber, is drawn through the fiberglass screen while on the vacuum box, a screen having smaller openings should be used. Alternatively, a piece of the tea bag material described below can be placed between the material and the screen and the final value adjusted for the fluid retained by the material as described below.

When the material to be tested is superabsorbent material, the test is run as set forth above with the following exceptions. A bag is prepared from heal sealable tea bag material (grade 542, commercially available from the Kimberley-Clark Corporation). A six inch by three inch sample of the material is folded in half and heat sealed along two edges to form a generally square pouch. 0.2 grams of the superabsorbent material to be tested (in the form of particles having a size within the range of from about 300 to about 600 μm, and a moisture content of less than about 5 weight percent) is placed in the pouch and the third side is heat sealed. The test is performed as described with the amount of the fluid absorbed by the bag material being subtracted from the amount of fluid retained by the bag and superabsorbent material. The amount of fluid absorbed by the bag material is determined by performing the saturated retention capacity test on an empty bag.

Fluid Intake Flowback Evaluation Test

Figure 4:
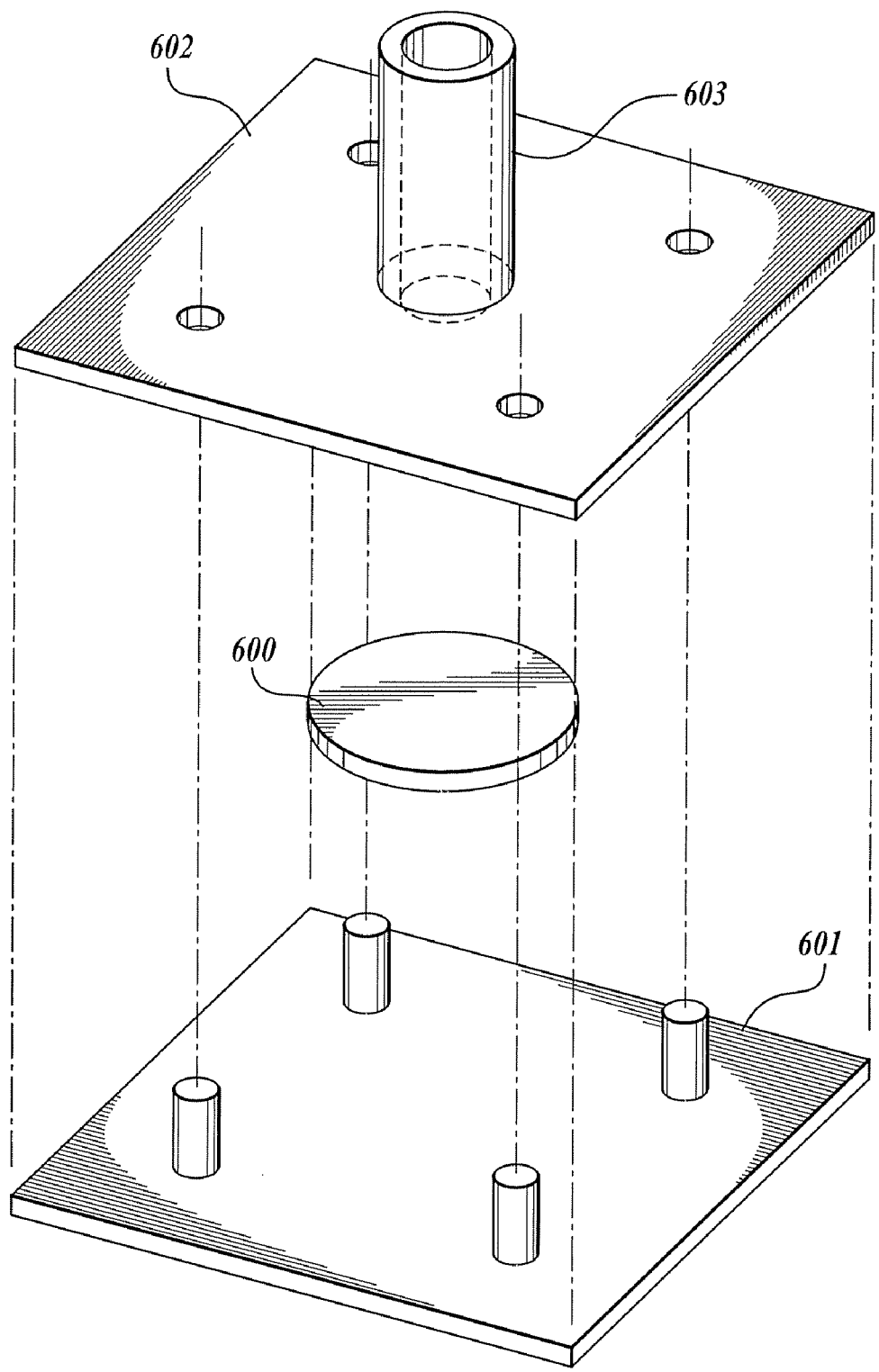
FIG. 4 is a device for conducting fluid intake flowback evaluation.

The fluid intake flowback evaluation (FIFE) test determines the amount of time required for an absorbent composite to intake a predetermined amount of liquid. A suitable apparatus for performing the FIFE test is shown in FIG. 4.

The samples for testing are prepared from fibers to be tested by distributing by hand approximately 2.5 g fiber into a 3 inch circular mold to form a uniform pad. A plunger is placed on top of the pad and the pad pressed to a final caliper of approximately 2.5 mm. The 3 inch circular pads including forming tissue on the top and bottom of the pad sample (composite 600).

Composite 600 is centered on FIFE test plate 601. Top 602 is then placed onto plate 601 with composite 600 centered under insult cylinder 603. Top 602 weighs 360 g providing a testing load of 0.11 psi on the sample when top 602 is in place for the test. Plate 601 and top 602 with cylinder 603 are made from PLEXIGLAS (approximate dimensions of 7 inches×7 inches). Insult cylinder 603 has an inner diameter of one inch, a length sufficient to receive at least 15 g liquid, and provides for communication of liquid to composite 601.

Prior to testing, the sample (composite 601) is weighed and its weight recorded, and the sample's bulk is measured at 0.05 psi and recorded.

In the test procedure, the sample (composite 601) is centered on plate 601 and top 602 applied. Once the sample is in place and the apparatus assembled, 15 g of 0.9% saline (first insult) is added to cylinder 603. Time zero is the time that the liquid first contacts the sample. The first insult time is measured as the time required for the first added liquid to be absorbed by the sample (i.e., liquid level drops below upper forming tissue of sample). After 15 minutes, a second insult is delivered by adding 15 g of 0.9% saline (second insult) to the cylinder and the sample. The second insult time is measured as the time required for the second added liquid to be absorbed by the sample. After 30 minutes, the third insult (15 g of 0.9% saline) is delivered and the third insult time measured, and after 45 minutes, the fourth insult (15 g of 0.9% saline) is delivered and the fourth insult time measured.

The following examples are provided for the purposes of illustrating, not limiting, the present invention.

EXAMPLES

Example 1

The Preparation of Pre-Crosslinked Pulp

In this example, the preparation of crosslinked cellulosic pulp is described. The crosslinked cellulosic pulp can be used to make the carboxyalkyl cellulose fibers of the invention.

120 grams of never-dried northern kraft spruce (NKS) pulp (oven-dried (OD) weight is 40 grams) is mixed in a plastic bag with sodium hydroxide, if necessary, water for 10 minutes at 10% consistency. Liquid is then pressed from the pulp and collected. Crosslinking agent was added to the liquid and then mixed with pulp in the bag. The bag was heated at 85° C. in a water bath for 70 minutes. After reaction, the reacting mixture was diluted with deionized (DI) water, filtered, and repeated to obtain >25% consistency pre-crosslinked pulp for used for carboxymethyl cellulose (CMC) preparation.

Table 1 summarizes suitable crosslinking agents useful in making carboxyalkyl cellulose from crosslinked pulp.

TABLE 1

The preparation of crosslinked pulp useful for making carboxymethyl cellulose fibers.

| Sample | Water g | 10% NaOH g | Crosslinking agent | DS |
|---|---|---|---|---|
| Control | 280 | 0 | 0 | 0.94 |
| 1-1 | 280 | 8 | 8 g 10% DCP | 0.94 |
| 1-2 | 270 | 8 | 2 g 10% glycerol diglycidal | 0.94 |
| 1-3 | 270 | 8 | 2 g 10% PEGDE | 0.91 |
| 1-4 | 270 | 8 | 4 g 10% 1.4 butanediol diglycidal | 0.94 |
| 1-5 | 270 | 0 | 8 g 10% GA and 2 g 10% AS | 0.91 |

DS: degree of carboxyl group substitution
DCP: 1,3-dichloro-2-propanol.
PEGDE: poly(ethylene glycol diglycidal ether).
GA: glyoxal.
AS: aluminum sulfate ($Al_2(SO_4)_3 \cdot 18H_2O$).

Example 2

Morphology of the Representative Crosslinked Carboxymethyl Cellulose Fibers In this example, the morphology (e.g., twists) of representative crosslinked carboxyalkyl cellulose fibers of the invention is described.

The twists per millimeter were counted for the pulp or fiber samples in their dry condition and in wet condition in a seventy percent ethanol/water solution. The sample fibers were distributed on a microscope slide and the twist count per millimeter was performed by measuring the length of one hundred fibers and counting the number of twists on those fibers. A separate count of fibers with no twists was kept for computing the percent yield. The image analysis system was calibrated using a two millimeter American Optical scale mounted in glass on a microscope slide.

Twist nodes per millimeter=total number of twists/ sum of the lengths.

% Yield=100*(1−($T_n$/($T_n$+100))) where $T_n$ is the number of fibers without twists.

TABLE 2

Representative crosslinked carboxymethyl cellulose fiber morphology.

| Sample | Twist per mm | | % Yield | |
|---|---|---|---|---|
| | Dry | Wet | Dry | Wet |
| NKS Pulp | 3.00 | 2.08 | 96.15 | 85.47 |
| 2-1 | 3.81 | 2.58 | 72.46 | 53.76 |
| 2-2 | 5.35 | 2.66 | 85.47 | 60.98 |
| 2-3 | 4.19 | 2.65 | 76.34 | 59.52 |
| 2-4 | 3.18 | 2.68 | 79.37 | 53.48 |
| 2-5 | 3.01 | 2.16 | 68.97 | 60.61 |
| Average | 3.91 | 2.55 | 76.52 | 57.67 |
| Pilot crosslinked CMC fibers | 2.48 | 2.75 | 64.10 | 46.51 |
| Laboratory CMC fibers | 5.62 | 2.35 | 85.47 | 59.17 |

The crosslinked carboxymethyl fibers of the invention had higher twist counts than the starting pulp at dry or wet state. These fibers also had higher twist counts than starting carboxymethyl cellulose fibers when wet, but lower twist counts than the starting carboxymethyl cellulose fibers. The crosslinked carboxymethyl fibers of the invention maintained their twist when wet, while carboxymethyl cellulose fibers without crosslinking lose their twist counts. The crosslinked carboxymethyl fibers of the invention prepared by the pilot run (Pilot crosslinked CMC fibers) have lower dry twist count than starting pulp, the crosslinked carboxymethyl fibers of the invention prepared by laboratory methods, or the starting carboxymethyl cellulose fibers, but higher wet twist count than the starting pulp, the crosslinked CMC from lab, CMC, and lab CMC.

Example 3

The Preparation of Representative Crosslinked Carboxymethyl Cellulose Fibers and Pads Including the Fibers In this example, the preparation of representative crosslinked carboxymethyl cellulose fibers of the invention and pads including the fibers are described.

409 grams of never-dried carboxymethyl cellulose fibers from high alpha sulfite pulp (the carboxymethyl cellulose fibers were neutralized in 70/30 ethanol/water, filtered and washed with 70/30 ethanol/water, filtered, then washed with 100% ethanol and filtered to 409 grams) (oven dried 70 grams) was mixed in a solution containing 515 grams of ethanol, 960 grams of water, 53.6 grams AA or aluminum acetate dibasic/boric acid (boric acid as stabilizer, 33 percent by weight), and 4.0 grams of Sunrez 747 (a permanent crosslinker) for one hour. After the reaction, the slurry was filtered to obtain 240 grams of wet sample. The sample was pin mill fluffed to obtain fiber bundle. Part of the wet fiber bundle was oven dried at about 60° C. for one hour to obtain dry product fiber bundles (Sample 3-4 and 3-6). The same procedure was used for same carboxymethyl cellulose fibers with only 50% of aluminum acetate/boric acid used (Sample 3-5 and 3-7). The fibers were tested for aluminum (Al), and boron (B), and the pads from the fibers bundles were tested by FIFE. Control pads with commercial SAP and fluff (CF 416 or NB416) were made for FIFE test for comparison. All wet pads were tested for pad integrity. Pads 3-6 and 3-7 were made with a pad former.

Table 3 summarizes the absorbent properties of representative crosslinked carboxyalkyl cellulose fibers and pads made from the fibers, and fiber metal content.

TABLE 3

Crosslinked carboxymethyl cellulose fibers and pad properties.

| Sample | AA | Free Swell (g/g) | CRC (g/g) | \multicolumn{4}{c}{FIFE insult time (seconds)} | Wet Pad Strength | Al/B (ppm) |
|--------|------|------|------|-----|-----|-----|-----|----------|------------|
|        |      |      |      | T1  | T2  | T3  | T4  |          |            |
| 3-4    | 100% | 60   | 17   | 18  | 29  | 25  | 24  | strong   | 10700/1700 |
| 3-5    | 50%  | 50   | 20   | 90  | 70  | 67  | 58  | 3.4 N    | 7800/1100  |
| 3-6    | 100% | 60   | 17   | 16  | 48  | 59  | 75  | medium   | 10700/1700 |
| 3-7    | 50%  | 50   | 20   | 180 | 83  | 180 | 200 | 2.6 N    | 7800/1100  |

Example 4

Representative Crosslinked Carboxyalkyl Cellulose Fibers: Aluminum Subacetate

This example describes the treatment of carboxymethyl cellulose fibers with aluminum subacetate, an aluminum crosslinking agent prepared immediately prior to use, to provide crosslinked carboxyalkyl cellulose fibers. This example describes a method for crosslinking carboxyalkyl cellulose fibers with this aluminum crosslinking agent.

7.9 gram of aluminum sulfate hexadecahydrate was dissolved in 69.3 grams of water and 7 grams of calcium carbonate was added slowly with stirring. After completion of $CO_2$ evolution, 16 grams of acetic acid was added slowly with stirring until $CO_2$ release is complete. The mixture was stirred and set for overnight to form a clear solution over a white precipitate. The top layer solution was collected through filtration to obtain 67 grams of clear liquid with a pH of 4.2. Into the liquid, 86 grams of ethanol was added and another 14 grams of water was added. The final solution (MA) has a pH of 5.25. 16.5 gram of solution MA was mixed with 15 grams of ethanol/water (6/4 wt) solution in a spray bottle and the solution was sprayed evenly on 27 grams of never dried cotton linter carboxymethyl cellulose fibers with DS of 0.95 in a plastic bag (OD weight CMC is 10 grams). The carboxymethyl cellulose fibers with solution MA was mixed by hand for half an hour and then dried in a aluminum tray at 66° C. for one hour. The dried product fibers have 4000 ppm of aluminum and no detectable boron.

The solution MA has 1800 ppm of aluminum and no boron and an IR spectrum different from aluminum acetate stabilized with boric acid or aluminum acetate basic.

Example 5

Representative Crosslinked Carboxyalkyl Cellulose Fibers: Aluminum Monoacetate

This example describes the treatment of carboxymethyl cellulose fibers with aluminum subacetate, an aluminum crosslinking agent prepared immediately prior to use, to provide crosslinked carboxyalkyl cellulose fibers. This example describes a method for crosslinking carboxyalkyl cellulose fibers with this aluminum crosslinking agent.

Solution, Reagent and Admixture Preparations

The aluminum acetate solution used in this process is prepared by modification of the process described in United States Pharmacopoeia (26 p 93) for aluminum subacetate topical solution, described as the diacetate, $Al(O_2CCH_3)_2$ OH. In contrast, the solution described herein is for a solution described as the monoacetate, $Al(O_2CCH_3)(OH)_2$.

Aluminum acetate solution is prepared as follows:

Aluminum sulfate octadecahydrate (490 g) is dissolved in cold water (560 g, 1-10° C.). Calcium carbonate (244 g) is added in portions with mixing until a stiff slurry is formed. The slurry is diluted with 113 g cold water and any remaining $CaCO_3$ is added. Glacial acetic acid (256 mL) is added with stirring. The mixture is kept cold for 1-2 hours and then filtered under vacuum to give approximately 820 g solution (d=1.0996 g/mL at 20° C.). The concentration of aluminum acetate, dibasic in the solution is 23.4% (w/w). Other solutions of lower concentrations may be produced from this solution by weight/weight serial dilution. The salt solution is unstable to heat and must be kept cold. The best results are obtained if the solution is used within 4 hours.

The following is a balanced chemical reaction for the basic chemistry involved in making aluminum acetate solution:

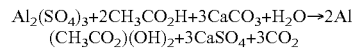

$Al_2(SO_4)_3 + 2CH_3CO_2H + 3CaCO_3 + H_2O \rightarrow 2Al(CH_3CO_2)(OH)_2 + 3CaSO_4 + 3CO_2$ The chemical reaction above is illustrative only, as the recipe uses more than three-times the equivalent amount of acetic acid called for by the stoichiometry given.

Reagents made from aluminum acetate solution are produced as follows:

Reagent 1: Concentrated (23.4% w/w) aluminum acetate, dibasic solution (226 g) is diluted with methanol (620 g) and denatured alcohol (250 g) to afford a cocktail containing 4.8% aluminum acetate, dibasic.

Reagent 2: Diluted (14% w/w) aluminum acetate, dibasic solution (247 g) is diluted with methanol (832 g) and denatured alcohol (325 g) to afford a cocktail containing 2.5% aluminum acetate, dibasic.

Admixtures of the carboxymethyl cellulose fibers and aluminum salts are produced as follows:

Example 5A

Three samples of carboxymethyl cellulose fibers prepared from NKS pulp (DS about 0.9-1.0) in denatured alcohol (13 g fibers and 53 g alcohol) were treated separately with 260-320 g of Reagent 1 in a container sized such that the fibers were completely immersed in the reagent. The mixtures were covered and allowed to stand with occasional stirring for 1 hour. The samples were suction filtered to give a series of samples with varying retention ratios (R) of 5, 4 and 3, where R=(total wet weight/(fibers-dry weight). The samples were partially dried in a convection oven equipped with an induced draft for 10-20 minutes at 66-68° C. The samples were then pin-milled and returned to the oven for another 60-80 minutes.

Example 5B

Three samples of carboxymethyl cellulose fibers in denatured alcohol, each containing 15 g fibers and 62 g alcohol, are treated separately with 280-350 g of Reagent 2 in a container sized such that the fibers were completely immersed in the reagent. The samples are worked up in identical fashion to those in Example 5A.

Example 6

The Preparation of Representative Crosslinked Carboxymethyl Cellulose Fibers from Crosslinked Cellulose Fibers In this example, the preparation of representative crosslinked carboxymethyl cellulose fibers of the invention are prepared by crosslinking carboxymethyl cellulose prepared from crosslinked cellulose.

The following examples describe the use of crosslinked pulp as a starting material for making carboxyalkyl cellulose (e.g., CMC) that is then further crosslinked (non-permanent crosslinks) to provide superabsorbent carboxyalkyl cellulose. The crosslinked pulp useful in making superabsorbent carboxyalkyl cellulose is crosslinked with a crosslinking agent that provides crosslinks that are stable to the alkaline conditions of the carboxyalkylation reaction. Suitable crosslinking agents include those that form ether crosslinks. Representative crosslinking agents that form ether crosslinks include 1,3-dichloro-2-propanol (DCP), divinyl sulfone (DVS), glycerol diglycidal, 1,4-butanediol diglycidal, and poly(ethylene glycol) diglycidal ether) (PEGDE).

Example 6A

The Preparation of Crosslinked Carboxymethyl Cellulose from 1,3-Dichloro-2-propanol Crosslinked Cellulose. In this example, the preparation of crosslinked carboxymethyl cellulose from carboxymethyl cellulose prepared from crosslinked pulp (1,3-dichloro-2-propanol crosslinked pulp) is described. In this method, carboxymethyl cellulose prepared from crosslinked pulp is crosslinked with aluminum acetate.

10 grams of air-dried CMC (DS 0.95) from never-dried crosslinked pulp (1,3-dichloro-2-propanol crosslinked pulp, Sample 1-1 in Example 1) was immersed in 100 grams of 75/25 ethanol/water solution with 3% aluminum acetate (dibasic, stabilized with boric acid) for 50 minutes. The slurry was filtered to a weight of 40 grams. The wet samples were then oven dried at 76° C. for 50 minutes (Sample 13A-1).

The same procedure was followed for a low DS CMC (DS 0.8) from a low consistency procedure (Sample 6A-2) and a low DS CMC sample (DS 0.6) from a high consistency procedure (Quantum mixer) (Sample 6A-3) (both control CMCs are from never-dried PA pulp without pre-crosslinking).

Table 4 summarizes the absorbent properties and metal contents of the product crosslinked carboxyalkyl celluloses.

TABLE 4

Representative crosslinked carboxymethyl cellulose fiber properties.

| Sample | Free swell (g/g) | CRC (g/g) | AUL (g/g) | Al ppm | B ppm |
|---|---|---|---|---|---|
| 6A-1 | 58 | 29 | 40 | — | — |
| 6A-2 | 46 | 26 | 29 | — | — |
| 6A-3 | 52 | 17 | 32 | 11350 | 1570 |

Example 6B

The Preparation of Crosslinked Carboxymethyl Cellulose from Glycerol Diglycidal Crosslinked Pulp. In this example, the preparation of crosslinked carboxymethyl cellulose from carboxymethyl cellulose prepared from crosslinked pulp (glycerol diglycidal crosslinked pulp) is described. In this method, carboxymethyl cellulose prepared from crosslinked pulp is crosslinked with aluminum acetate.

15 grams of air-dried CMC (DS 0.95) from never-dried crosslinked pulp (glycerol diglycidal crosslinked pulp, Sample 1-2 in Example 1) was immersed in 330 grams of 50/50 ethanol/water solution with 1.5% aluminum acetate (dibasic, stabilized with boric acid) for 50 minutes. The slurry was filtered to a weight of 60 grams. The wet sample was then oven dried at 76° C. for 50 minutes (Sample 6B-1, pH 6.1). The same procedure was applied to CMC with slurry pH adjustment (using NaOH) to provide Sample 6B-2 (pH 6.9) and Sample 6B-3 (pH 7.7).

Table 5 summarizes the absorbent properties and metal contents of the product crosslinked carboxyalkyl celluloses.

TABLE 5

Representative crosslinked carboxymethyl cellulose fiber properties

| Sample | Free Swell (g/g) | CRC (g/g) |
|---|---|---|
| 6B-1 | 54 | 12 |
| 6B-2 | 54 | 13 |
| 6B-3 | 49 | 22 |

Example 7

The Preparation of Representative Crosslinked Carboxymethyl Cellulose Fibers: Crosslinking with 1,3-Dichloro-2-propanol During Carboxyalkylation and Crosslinking with Aluminum Chloride Post-Carboxyalkylation This example describes the preparation of representative crosslinked carboxymethyl cellulose fibers of the invention that are prepared by two-stage crosslinking: (1) permanent crosslink formation using 1,3-dichloropropanol during carboxyalkylation and (2) non-permanent crosslink formation using aluminum chloride post-carboxyalkylation.

This example compares the absorbent properties of two representative crosslinked carboxyalkyl cellulose fibers of the invention: (1) crosslinked carboxyalkyl cellulose fibers that include non-permanent aluminum crosslinks and (2) crosslinked carboxyalkyl cellulose fibers that include non-permanent aluminum crosslinks and permanent ether crosslinks.

The example also demonstrates the effect of crosslinking agent amount, pulp degree of polymerization (DP), and carboxyalkyl cellulose degree of carboxyl group substitution (DS) on centrifuge retention capacity (CRC).

The first pulp was a lower alpha (86-88%), lower DP (1600-1700 ASTM) kraft fluff pulp designated NB416 manufactured by Weyerhaeuser Company (Pulp A in Table 7).

The second pulp was a high alpha (95%), high DP (2600 ASTM) sulfite dissolving pulp designated Olympic HV manufactured by Weyerhaeuser Company (Pulp B in Table 7).

In the method, the pulp was carboxymethylated with or without addition of 1,3,-dichloro-2-propanol (DCP), a crosslinking agent that provides permanent crosslinks. The crosslinking agent (0, 2, or 4 weight % based on oven-dried pulp) was added together with the monochloro acetic acid during the carboxymethylation process. Two levels of carboxymethylation (DS) were investigated: (1) 0.65-0.75 and (2) 0.95-1.00.

After the carboxymethylation reaction was complete, the CMC slurry was neutralized with acetic acid and then washed with ethanol/water mixtures to remove salt. The CMC was washed with 100% ethanol and filtered to a consistency of about 20%

The washed was then crosslinked (e.g., surface crosslinked with an amount of aluminum chloride (a crosslinking agent that provides non-permanent crosslinks)) in an ethanol/water slurry. The consistency of the slurry was about 5% and typically contains 60% ethanol and 40% water. The treated CMC was allowed to soak with the aluminum chloride for about 1 hour and filtered.

The product crosslinked carboxymethyl cellulose was dried in a forced-air oven at about 65° C. until partially dried and then removed and treated in a pin-fluffer to minimize clumpiness. The crosslinked carboxymethyl cellulose was then returned to the oven to complete the drying.

Once dry, the crosslinked carboxymethyl cellulose may be optionally heat treated at higher temperatures to increase the amount of crosslinking.

Absorbent capacity (CRC) generally decreased with increasing levels of permanent crosslinking and aluminum chloride treatment. As permanent crosslinking levels were increased, less aluminum chloride treatment was required to achieve a given CRC.

With Pulp A, the amount of CRC lost as the permanent crosslinking level is increased is minimal. A 4% permanent crosslinking level appears best for Pulp A. CRC decreases more rapidly with increased permanent crosslinking for Pulp B; a 2% permanent crosslinking level appears best.

CRC decreases with DS. CRC values are generally below 20 g/g for Pulp A at 0.75 DS. CRC values for Pulp B are also lower at 0.75 DS than at 0.95 DS, but remain above 20 g/g for lower aluminum chloride levels.

At low levels of permanent crosslinking and/or DS, Pulp B (higher DP and alpha pulp) has greater capacity levels than Pulp A (lower DP and alpha pulp). At higher levels of permanent crosslinking and high DS, Pulp A tends to have higher capacity.

The composition and absorbent properties (CRC) of representative crosslinked carboxyalkyl cellulose fibers of the invention are summarized in Table 7.

The following examples describe the preparation of representative crosslinked carboxyalkyl cellulose fibers of the invention.

Example 7A

The Addition of a Permanent Crosslinking Agent during the Preparation of Carboxymethyl Cellulose from Never-Dried Kraft Pulp. This example describes the preparation of carboxymethyl cellulose fibers by permanent crosslink formation using 1,3-dichloropropanol during carboxyalkylation.

Never-dried kraft pulp (200.0 g, oven dried NB416) was mixed with isopropanol (11.36 L) under nitrogen environment at 0° C. for 30 min. A sodium hydroxide solution (167.25 g in water with a total weight of 620.15 g) was added dropwise over 30 minutes and the reaction was left to stir for 1 h. A solution of monochloroacetic acid (181.50 g) and 1,3,-dichloro-2-propanol (8.0 g) in isopropanol (439 ml) was added dropwise to the stirring pulp over 30 min while the reaction temperature was increased to 55° C. The reaction was stirred for 3 h and then filtered, the filtered product was placed in 12 L 70/30 methanol/water solution, and neutralized with acetic acid. The resulting slurry was collected by filtration, washed one time each with 12 L 70/30, 80/20, and 90/10 ethanol/water solutions and then finally with 100% methanol or ethanol to provide the product crosslinked carboxymethyl cellulose (Sample 7A).

Example 7B

The Preparation of Carboxymethyl Cellulose from Never-Dried Kraft Pulp. This example describes the preparation of representative crosslinked carboxymethyl cellulose fibers of the invention that are prepared by non-permanent crosslink formation using aluminum chloride post-carboxyalkylation.

An aluminum chloride crosslinking solution was prepared by combining 143.9 g of 100% denatured ethanol, 131.93 grams of water and 0.408 g of aluminum chloride hexahydrate. To this solution were added 69.00 g of ethanol wet (21.74% solids) carboxymethylcellulose (prepared as described in Example 1). Based on these proportions, the active aluminum chloride applied to the CMC fiber was 1.5% and the ratio of ethanol to was 60% to 40%. The mixture of CMC fiber and crosslinking agent solution was mixed and then allowed to stand at room temperature for 1 hour. After standing the slurry was filtered to a weight 60.59 g. and then oven dried at 68° C. Mid-way through the drying the sample was pin-fluffed to minimize clumping and then returned to the oven until dry to provide crosslinked carboxymethyl cellulose fiber (Sample 7B).

Example 7C

The Addition of a Permanent Crosslinking Agent during the Preparation of Carboxymethyl Cellulose from Never-Dried Kraft Pulp. This example describes the preparation of representative crosslinked carboxymethyl cellulose fibers of the invention that are prepared by two-stage crosslinking: (1) permanent crosslink formation using 1,3-dichloropropanol during carboxyalkylation and (2) non-permanent crosslink formation using aluminum chloride post-carboxyalkylation.

An aluminum chloride crosslinking solution was prepared by combining 150.08 g of 100% denatured ethanol, 131.93 grams of water and 0.489 g of aluminum chloride hexahydrate. To this solution were added 62.81 g of ethanol wet (23.88% solids) carboxymethylcellulose (Sample 7A, prepared as described in Example 7A). Based on these proportions, the active aluminum chloride applied to the CMC fiber was 1.8% and the ratio of ethanol to was 60% to 40%. The mixture of CMC fiber and crosslinking agent solution was mixed and then allowed to stand at room temperature for 1 hour. After standing the slurry was filtered to a weight 58.03 g. and then oven dried 68 C. Mid-way through the drying the sample was pin-fluffed to minimize clumping and then returned to the oven until dry to provide a representative crosslinked carboxymethyl cellulose fiber of the invention (Sample 7C).

Table 6 summarizes the absorbent properties (CRC) of representative crosslinked carboxyalkyl cellulose fibers.

TABLE 6

Centrifuge retention capacities for representative crosslinked carboxymethyl cellulose fibers.

| Sample | CRC* (g/g) |
|---|---|
| 7B | 29.0 |
| 7C | 21.9 |

TABLE 7

Representative crosslinked carboxymethyl cellulose composition and centrifuge retention capacity.

| Sample | $AlCl_3$ (wgt % wgt CMC) | Pulp | CMC DS | DCP (wgt % wgt CMC) | CRC* (g/g) |
|---|---|---|---|---|---|
| 7-1 | 1.5% | A | 0.95 | 0% | 29.0 |
| 7-2 | 2.8% | A | 0.95 | 0% | 18.0 |
| 7-3 | 5.0% | A | 0.95 | 0% | 12.0 |
| 7-4 | 0.8% | A | 1.01 | 2% | 31.0 |
| 7-5 | 1.5% | A | 1.01 | 2% | 26.1 |
| 7-6 | 2.5% | A | 1.01 | 2% | 21.2 |
| 7-7 | 0.5% | A | 1.00 | 4% | 30.4 |
| 7-8 | 1.0% | A | 1.00 | 4% | 27.3 |
| 7-9 | 1.8% | A | 1.00 | 4% | 21.9 |
| 7-10 | 1.0% | B | 0.99 | 0% | 23.0 |
| 7-11 | 2.0% | B | 0.99 | 0% | 36.5 |
| 7-12 | 4.0% | B | 0.99 | 0% | 24.1 |
| 7-13 | 0.5% | B | 0.98 | 2% | 36.6 |
| 7-14 | 1.3% | B | 0.98 | 2% | 24.7 |
| 7-15 | 2.0% | B | 0.98 | 2% | 18.4 |
| 7-16 | 0.4% | B | 0.99 | 4% | 19.2 |
| 7-17 | 0.8% | B | 0.99 | 4% | 19.9 |
| 7-18 | 1.5% | B | 0.99 | 4% | 16.5 |
| 7-19 | 1.0% | A | 0.72 | 0% | 20.3 |
| 7-20 | 2.0% | A | 0.72 | 0% | 16.7 |
| 7-21 | 4.0% | A | 0.72 | 0% | 11.6 |
| 7-22 | 0.5% | A | 0.68 | 2% | 17.9 |
| 7-23 | 1.3% | A | 0.68 | 2% | 16.1 |
| 7-24 | 2.0% | A | 0.68 | 2% | 14.4 |
| 7-25 | 0.4% | A | 0.71 | 4% | 14.2 |
| 7-26 | 0.8% | A | 0.71 | 4% | 13.2 |
| 7-27 | 1.5% | A | 0.71 | 4% | 12.3 |
| 7-28 | 0.8% | B | 0.68 | 0% | 37.5 |
| 7-29 | 1.8% | B | 0.68 | 0% | 31.2 |
| 7-30 | 3.8% | B | 0.68 | 0% | 17.3 |
| 7-31 | 0.5% | B | 0.69 | 2% | 22.3 |
| 7-32 | 1.0% | B | 0.69 | 2% | 20.2 |
| 7-33 | 1.5% | B | 0.69 | 2% | 18.7 |
| 7-34 | 0.3% | B | — | 4% | 14.6 |
| 7-35 | 0.6% | B | — | 4% | 14.0 |
| 7-36 | 1.2% | B | — | 4% | 13.0 |

The Centrifuge Retention Capacity test values set forth in Tables 6 and 7 (CRC*) were determined by the following method.

The Centrifuge Retention Capacity (CRC) Test measures the ability of the absorbent sample to retain liquid therein after being saturated and subjected to centrifugation under controlled conditions. The resultant retention capacity is stated as grams of liquid retained per gram weight of the sample (g/g). For the fiber samples, the sample to be tested is used as is.

The retention capacity is measured by placing 0.2±0.005 grams of the sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two TEFLON coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag } wgt \text{ after centrifuge} - \text{empty bag } wgt \text{ after centrifuge} - \text{dry sample } wgt}{\text{dry sample } wgt}$$

The three samples are tested and the results are averaged to determine the centrifuge retention capacity (CRC). The samples are tested at 23±1 degrees Celsius at 50±2 percent relative humidity.

While illustrative embodiments have been illustrated and described, it will be appreciated that various changes can be made therein without departing from the spirit and scope of the invention.

The invention claimed is:

1. Substantially water-insoluble, water-swellable, non-regenerated, carboxyalkyl cellulose fibers, wherein the fibers have a surface having the appearance of the surface of a cellulose fiber, and wherein the fibers comprise a plurality of non-permanent intra-fiber metal crosslinks and a plurality of permanent intra-fiber crosslinks.

2. The fibers of claim 1, wherein the non-permanent intra-fiber metal crosslinks comprise multi-valent metal ion crosslinks.

3. The fibers of claim 2, wherein the multi-valent metal ion crosslinks comprise one or more metal ions selected from the group consisting of aluminum, boron, bismuth, titanium, zirconium, cerium, and chromium ions, and mixtures thereof.

4. The fibers of claim 1, wherein the non-permanent intra-fiber metal crosslinks comprise aluminum ions.

5. The fibers of claim 1, wherein the permanent intra-fiber crosslinks are selected from the group consisting of ether cross links and ester crosslinks.

6. The fibers of claim 1, wherein the permanent intra-fiber crosslinks comprise covalent crosslinks formed from an organic compound having at least two functional groups capable of reacting with at least one functional group selected from the group consisting of carboxyl, carboxylic acid, and hydroxyl groups.

7. The fibers of claim 6, wherein the organic compound is 1,3-dichloro-2-propanol.

8. Substantially water-insoluble, water-swellable, non-regenerated, carboxyalkyl cellulose fibers, wherein the fibers have a surface having the appearance of the surface of a cellulose fiber, and wherein the fibers comprise a plurality of non-permanent intra-fiber metal crosslinks and a plurality of permanent intra-fiber crosslinks, wherein the permanent intra-fiber crosslinks comprise covalent crosslinks formed from 1,3-dichloro-2-propanol.

9. The fibers of claim 8, wherein the non-permanent intra-fiber metal crosslinks comprise multi-valent metal ion crosslinks.

10. The fibers of claim 9, wherein the multi-valent metal ion crosslinks comprise one or more metal ions selected from the group consisting of aluminum, boron, bismuth, titanium, zirconium, cerium, and chromium ions, and mixtures thereof.

11. The fibers of claim 8, wherein the non-permanent intra-fiber metal crosslinks comprise aluminum ions.

12. A fiber bundle, comprising a plurality of substantially water-insoluble, water-swellable, non-regenerated, carboxyalkyl cellulose fibers, wherein the fibers have a surface having the appearance of the surface of a cellulose fiber, and wherein the fibers comprise a plurality of non-permanent intra-fiber metal crosslinks and a plurality of permanent intra-fiber crosslinks.

13. The fiber bundle of claim 12, wherein the non-permanent intra-fiber metal crosslinks comprise multi-valent metal ion crosslinks.

14. The fiber bundle of claim 13, wherein the multi-valent metal ion crosslinks comprise one or more metal ions selected from the group consisting of aluminum, boron, bismuth, titanium, zirconium, cerium, and chromium ions, and mixtures thereof.

15. The fiber bundle of claim 12, wherein the non-permanent intra-fiber metal crosslinks comprise aluminum ions.

16. The fiber bundle of claim 12, wherein the permanent intra-fiber crosslinks are selected from the group consisting of ether crosslinks and ester crosslinks.

17. The fiber bundle of claim 12, wherein the permanent intra-fiber crosslinks comprise covalent crosslinks formed from an organic compound having at least two functional groups capable of reacting with at least one functional group selected from the group consisting of carboxyl, carboxylic acid, and hydroxyl groups.

18. The fiber bundle of claim 17, wherein the organic compound is 1,3-dichloro-2-propanol.

* * * * *